(12) United States Patent
Muheim et al.

(10) Patent No.: US 6,235,507 B1
(45) Date of Patent: May 22, 2001

(54) MICROBIOLOGICAL PROCESS FOR PRODUCING VANILLIN

(75) Inventors: Andreas Muheim, Zürich; Bruno Müller, Dübendorf; Thomas Münch, Illnau; Markus Wetli, Forch, all of (CH)

(73) Assignee: Givaudan Roure (International) SA, Vernier-Geneve (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/096,230

(22) Filed: Jun. 11, 1998

(30) Foreign Application Priority Data

Jun. 19, 1997 (EP) .................................................. 97110010

(51) Int. Cl.⁷ ....................................................... C12P 7/24
(52) U.S. Cl. ............................ 435/147; 435/123; 435/155
(58) Field of Search ..................................... 435/147, 123, 435/155

(56) References Cited

U.S. PATENT DOCUMENTS

| | | |
|---|---|---|
| 4,874,701 | 10/1989 | Cooper . |
| 4,981,795 | 1/1991 | Cooper . |
| 5,128,253 | 7/1992 | Labuda . |

FOREIGN PATENT DOCUMENTS

| | | |
|---|---|---|
| 3604874 A1 | 8/1987 | (DE) . |
| 405 197 A1 | 1/1991 | (EP) . |
| 453 368 | 10/1991 | (EP) . |
| 542 348 A2 | 5/1993 | (EP) . |
| 761 817 A2 | 8/1996 | (EP) . |
| 2301103 A1 | 5/1995 | (GB) . |
| 5-227980 | 9/1993 | (JP) . |
| WO 96/34971 | 1/1996 | (WO) . |
| WO 96/08576 | 3/1996 | (WO) . |

OTHER PUBLICATIONS

Toms & Wood, *Biochemistry*, 9 (1970):337–43.
Sutherland, et al., *Can J. Microbiol.*, 29 (1983): 1253–57.
Pometto, et al., *Appl. Environ. Microbiol.*, 51, 171–179, 1986.*
Huang et al., Journal of Biological Chemistry, (1993) vol. 268, No. 32, pp. 23954–23958.*

\* cited by examiner

*Primary Examiner*—Irene Marx
(74) *Attorney, Agent, or Firm*—Mark E. Waddell; Stephen M. Haracz; Bryan Cave LLP

(57) ABSTRACT

A microbiological process for producing vanillin and other useful products from ferulic acid is disclosed. Vanillin and guaiacol are recovered from the process using a differential pH extraction where the guaiacol is recovered at a pH of greater than 9 and the vanillin is recovered at a pH of from about 5 to about 8.

8 Claims, 1 Drawing Sheet

MICROBIOLOGICAL PROCESS FOR PRODUCING VANILLIN

The present invention concerns a microbiological process for the production of vanillin from ferulic acid. According to this process, a culture, preferably a submerged culture, of any bacterium of the order Actinomycetales, preferably of the family Streptomycetaceae is incubated with the substrate ferulic acid to fermentatively produce vanillin. The product vanillin is recovered from the fermentation broth by a designed extraction method allowing also the separation and recovery of valuable fermentation by-products, in order to obtain the analytically and sensorically purified product vanillin, and, in particular the by-product guaiacol.

BACKGROUND

In the use of flavouring compounds, it is more and more important that the flavour compounds can be designated as "natural". In line with the European and U.S. regulations this means that the compound has to be obtained by physical, enzymatic or microbiological processes and only from materials of plant or animal origin. Various research activities during the last decade were thus focused on the use of renewable, cheap and natural raw material sources for the fermentative production of vanillin. However, commercially attractive volumetric yields have not as yet been reported so far.

Guaiacol is a phenolic, smoky type of molecule which significantly contributes to the characteristic flavour of vanilla extracts. It is thus often used in combination with vanillin for vanilla type flavours. However, the fermentative production of natural guaiacol has not yet been described so far.

In the past 10 years, several methods concerning the microbial or enzymatic production of vanillin have been proposed. In general, a suitable precursor is transformed to vanillin by a microorganism or an enzyme. Suggested precursors are eugenol, isoeugenol, ferulic acid, curcumin or benzoe siam resins. Usually, transformation yields are extremely low. For example, Haarman & Reimer (EP 0 405 197 A1) describe a production of 18 mgL$^{-1}$ starting from 0.2 gL$^{-1}$ eugenol using the microorganisms Serratia, Klebsiella or Enterobacter. This transformation takes place over a period of 13 days. Pernod-Ricard (EP 453 368 A) describe a process where 46 mgL$^{-1}$ vanillin was obtained in a 6 day Pycnoporus fermentation from ferulic acid. Along this line is also Kraft General Foods (U.S. Pat. No. 5,128,253) describing a process where 210 mgL$^{-1}$ vanillin is obtained from ferulic acid within 54 days. In order to obtain this titer a reducing agent had to be added as otherwise the formation of vanillin would not occur and only vanillic acid would be formed. Takasago (JP 227980/1993) prepared mutants of Pseudomonas strains that are blocked in the degradation pathway of vanillin. Thus, starting with 1 gL$^{-1}$ ferulic acid 0.28 gL$^{-1}$ vanillin could be obtained. An application reporting a potentially economical attractive volumetric yields of vanillin in a fermentation process has recently been published by Haarman, & Reimer (EP 0 761 817 A2). They identified two strains of the genus Amycolatopsis which are able to accumulate vanillin up to a concentration of 11.5 gL$^{-1}$ in the fermentation broth after feed of ferulic acid.

It can be concluded from the above discussion that high amounts of vanillin are not easily formed in microbial systems. This is mainly due to the cellular toxicity of vanillin, which at concentrations above 1 gL$^{-1}$ prevents growth of the vanillin producing microorganisms. In microbial systems, usually the respective alcohol or acid is found and not vanillin. This toxic effect of vanillin was overcome by the use of enzymes (Quest, EP 0 542 348 A2). Treating isoeugenol with lipoxygenase resulted in 10–15 gL$^{-1}$ vanillin at a yield of 10–15%. Much lower concentrations were obtained when using eugenol (0.3–0.5 gL$^{-1}$ in a yield of 0.3–0.5%) and no turnover is reported for ferulic acid. The method employing lipoxygenase is scarcely attractive from the economic point of view.

Another measure to circumvent the toxicity of this compound is the microbial production of coniferylaldehyde which forms vanillin upon thermal treatment. See, for example, BASF (Offenlegungsschrift, DE 3604874 A1). Similar is also the immobilized cell system recently described in WO 96134971 in which vanillin is accumulated up to a concentration of 1 gL$^{-1}$. A possible economic benefit of using immobilized biomass is given by recycling the biocatalyst.

Many papers deal with the respective metabolic pathways starting from eugenol, isoeugenol or ferulic acid. In general, vanillin is believed to be an intermediate compound in the degradation pathway of these compounds. Two publications have discussed the involvement of vanillin in the degradation of ferulic acid. Toms and Wood, Biochemistry 9 (1970) 337–43, cultivated Pseudomonas sp. on ferulic acid and elucidated the degradation pathway. Though vanillin was not found in the culture supernatant, evidence was given that vanillin is an intermediate compound, since vanillic acid could be detected. Starting from ferulic acid, vanillin was obtained in cultures of *Streptomyces setonii* (Sutherland et al., Can. J. Microbiol. 29 (1983) 1253–57). No indication was given on the amount, but only traces where found when repeating the experiment.

Ferulic acid as a substrate for biotransformations is abundantly available from different natural sources. The acid often occurs in the form of a glucoside in plant materials, such as wood, sugar beet melasse, bran of corn, rice and various types of grasses. It can be isolated from the corresponding glycosides in these products by well-known hydrolysis methods, e.g. using enzymes, and can be used as crude material or purified material. A British source (GB 2301103 A1) describes for instance the enzymatic breakdown of ferulic acid containing plant material by a ferulic acid esterase, in order to obtain the free acid.

SUMMARY OF THE INVENTION

The present new, high-yield microbiological process for the production of vanillin contemplated by the present invention comprises cultivating first in a nutrient broth a microorganism of the order of the Actinomycetales, preferably of the family Streptomycetaceae, most preferably the bacterium *Streptomyces. setonii* ATCC 39116, wherein, preferably, the cultivating period is about 5–40 hours and lasts, until the carbon source glucose is (almost) consumed, then adding the substrate ferulic acid in the range of about 5–40 gL$^{-1}$ of fermentation broth, either continuously or batch-wise. After an approximate incubation (biotransformation) period of about 5–50 hours, substrate conversion to vanillin and several by-products is completed. The ferulic acid is consumed and vanillin accumulated up to about 8–16 gL$^{-1}$ in the fermentation broth. Typical by-products of the ferulic acid biotransformation are vanillic alcohol, vanillic acid, guaiacol, para-vinylguaiacol and 2-methoxy-4-ethyl-phenol.

Subsequent product recovery consists in the removal of the biomass, conveniently followed by a two-step extraction with an appropriate organic solvent, preferably methyl-tert-butylether. A first extraction is carried out at a pH of greater than about 9, preferably at a pH of from about 10 to about 11 and most preferably from about 10.8 to about 11 in the aqueous phase to selectively extract by-products, such as the sensorically highly active guaiacol. Then, the aqueous raffinate is "acidified" to neutral pH values a pH from about 5 to about 8; preferably from about 6 to about 7.5, most preferably from about 6.9 to about 7.1 to selectively extract the product vanillin. Purification of the raw vanillin extract may finally be done by applying well-known recrystallization methods. Guaiacol may be purified from the raw extract by distillation.

DETAIL DESCRIPTION OF THE INVENTION

Figure 1:
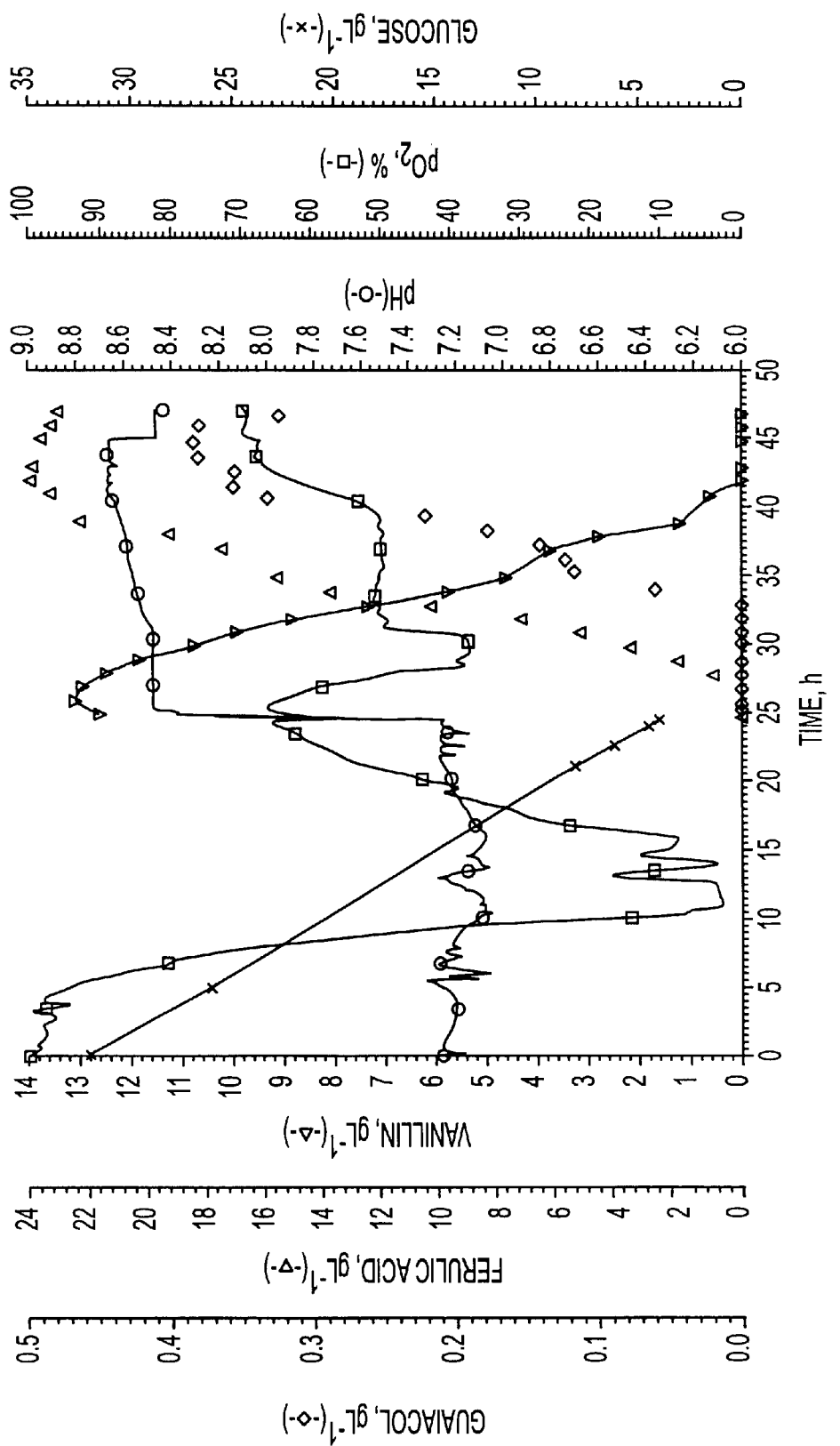
FIG. 1 shows a typical chart of a vanillin production batch at the 10 L scale. -△-vanillin concentration [$gL^{-1}$]; -▽-ferulic acid concentration [$gL^{-1}$]; -◇-guaiacol concentration [$gL^{-1}$]; -o-pH value; -□-$PO_2$ value [%]; -x-glucose concentration [$gL^{-1}$]. After a 24 hours growth phase the pH was adjusted to 8.5 before the ferulic acid was fed. 3–4 hours after the substrate addition, a small amount of vanillin was detected. A vanillin concentration of 13.9 $gL^{-1}$ was reached after totally 41 hours of fermentation (17 hours after the ferulic acid feed). At that time, a guaiacol concentration of 0.38 $gL^{-1}$ was measured. A production rate of 1.10 $gL^{-1}h^{-1}$ for vanillin and of 0.04 $gL^{-1}h^{-1}$ for guaiacol were calculated respectively. After complete conversion of ferulic acid, a decrease in the concentrations of vanillin and guaiacol was observed. Quantitative measurements were carried out by high performance liquid chromatography and gas chromatography.

The present new, high-yield microbiological process for the production of vanillin contemplated by the present invention comprises cultivating first in a nutrient broth a microorganism of the order of the Actinomycetales, preferably of the family Streptomycetaceae, most preferably the bacterium *Streptomyces setonii* ATCC 39116, wherein, preferably, the cultivating period is about 5–40 hours and lasts, until the carbon source glucose is (almost) consumed, then adding the substrate ferulic acid in the range of about 5–40 $gL^{-1}$ of fermentation broth, either continuously or batch-wise. After an approximate incubation (biotransformation) period of about 5–50 hours, substrate conversion to vanillin and several by-products is completed. The ferulic acid is consumed and vanillin accumulated up to about 8–16 $gL^{-1}$ in the fermentation broth. Typical by-products of the ferulic acid biotransformation are vanillic alcohol, vanillic acid, guaiacol, para-vinylguaiacol and 2-methoxy-4-ethyl-phenol.

Subsequent product recovery consists in the removal of the biomass, conveniently followed by a two-step extraction with an appropriate organic solvent, preferably methyl-tert-butylether. A first extraction is carried out at a pH of greater than about 9, preferably at a pH of from about 10 to about 11 and most preferably from about 10.8 to about 11 in the aqueous phase to selectively extract by-products, such as the sensorically highly active guaiacol. Then, the aqueous raffinate is "acidified" to neutral pH values a pH from about 5 to about 8; preferably from about 6 to about 7.5, most preferably from about 6.9 to about 7.1 to selectively extract the product vanillin. Purification of the raw vanillin extract may finally be done by applying well-known recrystallization methods. Guaiacol may be purified from the raw extract by distillation.

The microbiological process and the extraction procedure described are useful for the economically attractive production of natural vanillin as well as by-products from ferulic acid according to the following biochemical pathway:

Pathway of Ferulic Acid Degradation, e.g. by *Streptomyces setonii*

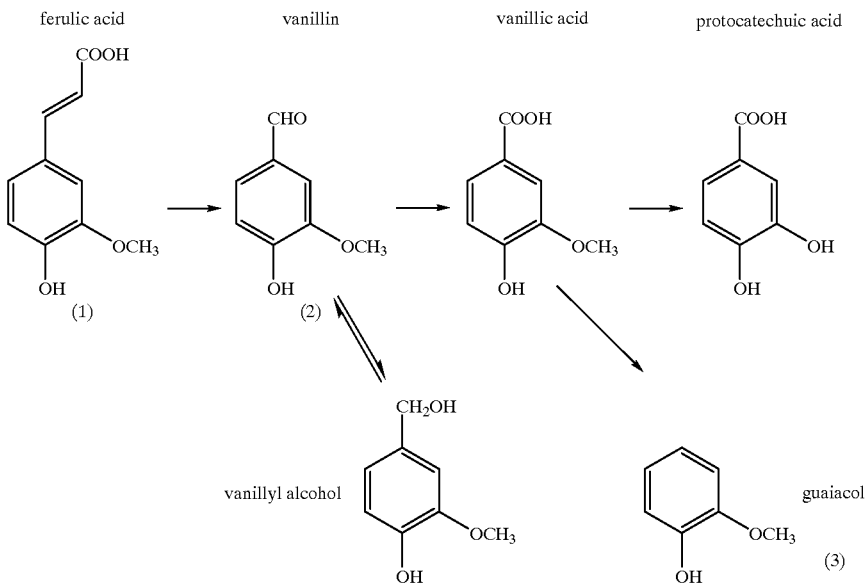

The resulting vanillin (compound 2) as well as the by-product guaiacol (compound 3) are both known flavour and fragrance compounds. Their use and application are well-known to those of ordinary skill in the art. By using effective and balanced amounts of these compounds, it is possible to augment or enhance the organoleptic properties of flavoured consumables, such as beverages, dairy products, baked goods, ice cream and the like. Fermentatively produced vanillin and guaiacol are especially valuable in any vanilla-type and fruit flavour compositions where entirely natural ingredients are required.

As pointed out above, exact fermentation conditions combined with an effective product recovery method have now been discovered to allow a high yield production of sensorically and analytically purified vanillin as well as getting the high-impact flavour compound guaiacol as a by-product. These conditions are based upon the cultivation of the bacterium of the genus Streptomyces in an appropriate culture medium and the subsequent addition of the substrate ferulic acid at excess concentrations, that is about 5 to about 40 g/l, to obtain vanillin at high volumetric yields in the fermentation broth.

Most suitable is, as pointed out above, the species *Streptomyces setonii*, preferably the strain ATCC 39116.

The substrate ferulic acid is defined by formula (1). According to the novel process a ferulic acid material with a ferulic acid content of, preferably, more than 10% is used as substrate. The nature of the remaining compounds is depending on the source.

In carrying out the present invention, cultivation of the bacterium is carried out in an aqueous medium in the presence of usual nutrient substances. A suitable culture medium contains a carbon source, an organic or inorganic nitrogen source, inorganic salts and growth factors.

For the culture medium, glucose is preferably used as the carbon source, e.g. at a concentration of about 5–50 $gL^{-1}$, preferably about 20–35 $gL^{-1}$. Yeast extract is a useful source of nitrogen, phosphates, growth factors and trace elements may be added, e.g. at preferred concentration of about 2–20 $gL^{-1}$, most preferably about 5–10 $gL^{-1}$. In addition, magnesium ions, e.g. magnesium sulfate may be added at a concentration of about 0.1–5 $gL^{-1}$, preferably at about 0.5–1 $gL^{-1}$.

The culture broth is prepared and sterilized in a bioreactor, and is then inoculated with a Streptomyces strain in order to initiate the growth phase. An appropriate duration of the growth phase is about 5–40 hours, preferably about 15–35 hours and most preferably about 20–30 hours.

Specifications of further process conditions are:

| pH-range: | about 7 to about 9 |
|---|---|
| temperature range: | about 30 to about 45° C. |
| aeration: | is preferred for this aerobic process |
| stirring: | is preferred. |

After the termination of the growth phase, the substrate ferulic acid is fed to the culture. A suitable amount of substrate-feed is 5–40 $gL^{-1}$ of fermentation broth, preferably about 15–30 $gL^{-1}$, most preferably 20–25 $gL^{-1}$. The substrate is either fed as solid material or as aqueous solution or suspension. The total amount of substrate is either fed in one step, in two or more feeding-steps, or continuously.

The biotransformation phase starts with the beginning of the substrate feed and lasts about 5–50 hours, preferably 10–30 hours and most preferably 15–25 hours, namely until all substrate is converted to product and by-products.

It is assumed that an excess concentration of the fed ferulic acid is mainly responsible for the high volumetric yield of vanillin as observed after the terminated substrate conversion. In addition, the process conditions outlined above are also assumed to be responsible for the accumulation of the valuable material guaiacol.

After the terminated biotransformation phase, the biomass is separated from the fermentation broth by any well known method, such as centrifugation or membrane filtration and the like to obtain a cell-free fermentation broth.

Since the biotransformation converts the hydrophilic substrate ferulic acid into rather hydrophobic substances such as vanillin and guaiacol, the overall volumetric productivity of the fermentation system might be increased by applying any in-situ product recovery method. For this purpose, e.g. an extractive phase can be added to the fermentation broth using, e.g. a water —immiscible—organic solvent, a plant oil or any solid extractant, e.g. a resin preferably, neutral resin such as Amberlite XAD 4 or XAD 7 or the like. Such an in-situ product recovery method might allow continuing formation of vanillin and guaiacol also after having reached the water solubility concentrations.

From this fermentation broth, vanillin and the by-products may now be extracted selectively by two different extraction methods:

Continuous liquid—liquid extraction a) or batch wise extraction b) are suitable.

a) On the basis of an extraction dependent on the pH value, an efficient isolation of vanillin and also of guaiacol can be carried out. In a first step, guaiacol can be extracted from an aqueous fermentation broth. For this step, a counter-current extraction method is preferably used, preferably in a extractor, by means of an organic water insoluble solvent. Examples of solvents are esters of $C_{1-3}$ acids with $C_{1-4}$-alcohols, ethers, in particular methyl tert-butyl ether (MTBE). The extraction occurs at a pH greater than 9, preferably between about 10 to about 11, in particular between about pH 10.8 to about 11.

Vanillin is thereafter extracted from the aqueous raffinate of the guaiacol extraction by having the pH values of the raffinate to about 5 to about 8, preferably from about 6 to about 7.5, and most preferably between about 6.9 to about 7.1.

Working with vanillin concentrations of about 8 to about 16 g/l, the counter current extraction operates most suitably in a ratio of feed/solvent of about 2.5–3:1, in particular about 2.6:1.

b) At higher concentrations of vanillin in the aqueous phase, e.g. after a concentration of the fermentation broth by means of water evaporation, a corresponding two-step batch-wise extraction at different pH values and with the solvents proposed above is suitable, and preferable.

The advantages of the novel process can be summarized as follows:

(1) Fermentation conditions are available which enable the accumulation of vanillin in the fermentation broth of Streptomyces, e.g. *S. setonii* to economically attractive concentrations (about 8–16 $gL^{-1}$).

(2) The process enables the simultaneous production of vanillin and guaiacol, that is two products of high value in the natural flavour preparation.

(3) The fermentation process is of low technical complexity and uses raw materials from easily accessible sources.

Finally, the invention concerns also the novel process for the manufacture of vanillin, but using instead of *Streptomyces setonii* ATCC 39116, its enzymes or any recombinant microorganisms, e.g. yeast, which contain the genetic material coding for the enzymes which are relevant or involved in the cellular biosynthesis of vanillin and/or guaiacol—and thus not the microoroganism as such.

EXAMPLE 1

250 mL shake flasks containing 50 mL of the following medium were prepared: 103 $gL^{-1}$ sucrose, 4 $gL^{-1}$ $Na_2HPO_4$, 1 $gL^{-1}$ $KH_2PO_4$, 1 $gL^{-1}$ yeast extract, 0.2 $gL^{-1}$ NaCl, 0.2 $gL^{-1}$ $MgSO_4$ and 0.05 $gL^{-1}$ $CaCl_2$. The pH was adjusted to 7.2 using NaOH. A shake flask was inoculated with 2 mL of reculture of *Streptomyces setonii* ATCC 39116 and cultivated at 37° C., 190 rpm or 16 hours. At the end of the growth phase 0.3 g ferulic acid (purchased from Aldrich, cat. no. 12.870–8, 99%) was added to the culture. For this purpose a 10% w/w solution of the acid substrate in 0.5 M NaOH (final pH of the solution was approximately 7.2) was previously prepared and sterile-filtered. The flask was incubated again at 37° C., 190 rpm. After 31.5 hours of biotransformation (incubation) a vanillin concentration of 3.10 $gL^{-1}$ (HPLC) was reached. A molecular yield of 66 mol % was calculated.

EXAMPLE 2

A 250 mL shake flask was prepared and incubated as in Example 1. After a 16 hours growth phase 0.6 g ferulic acid (as a 10% w/w solution in 0.5 M NaOH) was added to the culture. The flask was incubated again at 37° C. and 190 rpm. After 78 hours of biotransformation (incubation) a vanillin concentration of 5.94 $gL^{-1}$ (HPLC) was reached, corresponding to a yield of 63 mol %.

EXAMPLE 3

A 250 mL shake flask was prepared and incubated as in Example 1. After a 18 hours growth phase 0.3 g ferulic acid (as a 10% w/w solution in 0.5 M NaOH) was added to the culture. The flask was incubated again at 37° C. and 190 rpm. After 28 hours a second feed of 0.3 g ferulic acid followed. At the end of the incubation (58 hours) a vanillin concentration of 6.41 $gL^{-1}$ was reached, corresponding to a yield of 68 mol %.

EXAMPLE 4

A preculture of *Streptomyces setonii* was grown in a shake flask at pH 7.2, 37° C., 190 rpm, for 24 hours. The shake flask medium contained 5 $gL^{-1}$ glucose, 4 $gL^{-1}$ $Na_2HPO_4$, 1 $gL^{-1}$ $KH_2PO_4$, 10 $gL^{-1}$ yeast extract, and 0.2 $gL^{-1}$ $MgSO_4$.

A bioreactor was filled with 10 L of a medium containing 32 $gL^{-1}$ glucose, 8 $gL^{-1}$ yeast extract, 0.8 $gL^{-1}$ $MgSO_4$ and 0.2 $gL^{-1}$ antifoam agent (Dow Corning AF 1520). After thermal sterilization the reactor was inoculated with the previously grown shake flask preculture. The amount of inoculum used was 3%. The process conditions were 37° C., pH 7.2, airflow rate 1.0 vvm, 800 rpm. After 24 hours of growth phase a remaining glucose concentration of 4.6 $gL^{-1}$ was measured. Subsequently, the pH was shifted to 8.5 using NaOH (30%) and 24.5 hours after inoculation 2.25 L of a 10% w/w solution of ferulic acid in 0.5 M NaOH was added to the fermentation broth. At the time of the feed, the glucose concentration was down to 4.0 $gL^{-1}$. 3–4 hours after the addition of the precursor the beginning of the biotransformation of ferulic acid to vanillin was observed. 17 hours after the precursor feed, concentrations of 13.9 $gL^{-1}$ vanillin and 0.4 $gL^{-1}$ guaiacol were measured in the fermentation broth by gas chromatography. At that time, the ferulic acid was completely converted. A yield of vanillin of 75 mol % was calculated.

The bioprocess was then terminated by pasteurization at 80° C. for 15 minutes. The fermentation broth was microfiltered (0.2 μm).

EXAMPLE 5

A 450 L bioreactor with a working volume of 340 L was run according to the procedure described in the previous example.

After a growth period of 26.5 hours the pH was shifted to 8.5 and a first ferulic acid feed amounting to 4.08 kg was carried out according to Example 4. At that time a remaining concentration of 7.5 $gL^{-1}$ glucose was measured. 1 hour later a another 3.57 kg of precursor was fed. The total amount of ferulic acid addition was 22.5 $gL^{-1}$. 25.5 hours after the first precursor feed a vanillin concentration of 9.0 $gL^{-1}$ was measured. The ferulic acid concentration was now 1.75 $gL^{-1}$. A yield of vanillin of 51 mol % was obtained.

EXAMPLE 6

Liquid-liquid countercurrent extraction of vanillin and guaiacol at technical scale.

7930 kg of cell-free, membrane-filtered fermentation broth containing 7.1 $gL^{-1}$ vanillin and 0.35 $gL^{-1}$ guaiacol were adjusted to pH 11 with NaOH and extracted first with MTBE as solvent in a stirred-chamber counter current extractor to separate the guaiacol. After MTBE evaporation, 8 kg of raw extract containing MTBE and 33% w/w guaiacol were recovered. The pH of the aqueous raffinate of this alkaline extraction was then shifted to 6.9–7.1 with hydrochloric acid and again extracted with MTBE in the same extractor to separate the vanillin. From this second extraction step, 150 kg of a raw extract containing MTBE and 37% w/w vanillin were obtained.

What is claimed is:

1. A process for producing vanillin by conversion of ferulic acid comprising:
   a) cultivating a *S. setonii* microorganism in a nutrient broth for about 5 to about 40 hours to yield a cultivated nutrient broth;
   b) adding ferulic acid to the cultivated nutrient broth to form a broth having a concentration of ferulic acid of from about 5 g/L to about 40 g/L;
   c) incubating the ferulic acid-containing cultivated nutrient broth from about 5 to about 50 hours to form vanillin; and
   d) recovering the vanillin formed in step c).

2. The process according to claim 1, wherein guaiacol is also formed in incubation step c).

3. The process according to claim 2, wherein the guaiacol and vanillin are recovered by extraction from the broth of step c) comprising the steps of:
   $d_1$) increasing the pH of the broth in step c) to greater than 9.0;
   $d_2$) extracting the guaiacol with an organic water insoluble solvent;
   $d_3$) decreasing the pH of aqueous phase of step $d_2$) to from about 5 to about 8; and
   $d_4$) extracting the vanillin with an organic water insoluble solvent.

4. The process according to claim 3, wherein the pH for extracting the guaiacol is from about 10 to about 11.

5. By The process according to claim 3, wherein the pH for extracting the vanillin is from about 6 to about 7.5.

6. The process according to claim 3, wherein the extraction of guaiacol and vanillin is performed by continuous liquid—liquid extraction.

7. The process according to claim 3, wherein the extraction of guaiacol and vanillin is performed batch-wise.

8. The process of claim 1 wherein the *S. setonii* microorganism is *S. setonii* ATCC 39116.

\* \* \* \* \*